United States Patent [19]
Baker et al.

[11] Patent Number: 5,488,153
[45] Date of Patent: Jan. 30, 1996

[54] PROCESS FOR THE CARBONYLATION OF METHANOL OR A REACTIVE DERIVATIVE THEREOF

[75] Inventors: Michael J. Baker, Twickenham; Jonathan R. Dilworth, Colchester; John G. Sunley, Cottingham; Nigel Wheatley, Colchester, all of England

[73] Assignee: BP Chemicals Limited, London, England

[21] Appl. No.: 262,955

[22] Filed: Jun. 21, 1994

[30] Foreign Application Priority Data

Jun. 30, 1993 [GB] United Kingdom ............ 9313514
Apr. 14, 1994 [GB] United Kingdom ............ 9407363

[51] Int. Cl.$^6$ .......... C07C 51/12; C07C 67/36; C07F 15/00; B01J 31/00
[52] U.S. Cl. .......... 562/519; 556/18; 556/20; 560/232; 568/14; 568/15; 502/166
[58] Field of Search .......... 562/519; 560/232; 568/14, 15; 556/18, 20

[56] References Cited

U.S. PATENT DOCUMENTS

| 4,668,809 | 5/1987 | Oswald et al. ............ 556/18 |
| 4,670,570 | 6/1987 | Wegman et al. ............ 556/18 |
| 4,687,874 | 8/1987 | Oswald et al. ............ 568/454 |

FOREIGN PATENT DOCUMENTS

| 0114703 | 8/1984 | European Pat. Off. . |
| 0280380 | 8/1988 | European Pat. Off. . |
| 1401930 | 5/1965 | France . |
| 4121959 | 1/1993 | Germany . |
| 14121959 | 7/1993 | Germany . |
| 9204118 | 3/1992 | WIPO . |

OTHER PUBLICATIONS

Bressan et al., Journal of Organometallic Chemistry, vol. 247, pp. C8–C10 (1983).
Journal of the American Chemical Society, vol. 111, No. 6, 15 Mar. 1989, Washington DC US.
E. Block et al. '2-Phosphino-and 2-Phosphinylbenzenethiols: New Legend Types'—The Whole Document.
Dirasat: Nat. Sci. (Univ. Jordan) 1983, 10 47–55, H. A. Hodali et al.
Can. J. Chem. 1988, 66 1272, D. E. Berry et al.
J. Am. Chem. Soc. 1989, 111 2327–2329, E. Block et al.
J. Chem. Soc. Dalton Trans 1979, 1595–99, J. Chatt et al.
Inorg. Chem. 1993, 32 5676–5681.
Chemical Abstract, 119 (23):250133d., L. Zhang et al (1993).
Chemical Abstract 119(2):19212t. R. Contreras et al. (1993).
Chemical Abstract 117(25):251523b, J. Browning et al. (1992).
Chemical Abstract 115(25):280234x, S. Grim et al (1991).
Chemical Abstract 115(9):92586q, J. Browning et al. (1991).
Chemical Abstract 115(7):71862m, S. Grim et al (1991).
Chemical Abstract 115(3):29578y, M. S. Abbassioun et al (1991).
Inorg. Chim. Acta 154(1), 41–3, C. Bonuzzi et al., (1988).
Can. J. Chem. 64(9), 1870–5, D. G. Dick et al., (1986).
Can. J. Chem. 61(9), 2214–19, A. R. Sanger, (1983).
Inorg. Chim. Acta 53(3) L123–L124, A. R. Sanger, (1981).
PhD Thesis, 1992, (Abstract; Chapter 4; p. 158) Y. Zheng.
Inorg. Chim. Acta 1983, 77 L 139–L142, M. Bressan et al.
Inorg. Chim. Acta 1988, 146 89–92, G. K. Anderson et al.
Organometallics 1992, 11 20–22, C. Pisano et al.
J. Catal 1977, 47 269–271, K. M. Webber et al.
J. Chem Soc. Chem. Comm 1987, 1891, R. W. Wegman et al.

Primary Examiner—Porfirio Nazario-Gonzales
Attorney, Agent, or Firm—Brooks Haidt Haffner & Delahunty

[57] ABSTRACT

A process or the liquid phase carbonylation of methanol or a reactive derivative thereof comprises contacting carbon monoxide with a liquid reaction composition comprising methanol or a reactive derivative thereof, a halogen promoter and a rhodium catalyst system comprising a rhodium component and a bidentate phosphorus-sulphur ligand, the ligand comprising a phosphorus dative center linked to a sulphur dative or anionic center by a substantially unreactive backbone structure comprising two connecting carbon atoms or a connecting carbon and a connecting phosphorus atom. Novel rhodium ligand complexes of formula $[Rh(CO)L]_m$ and $Rh(CO)LY]$ wherein Y is a halogen, m is a number less than 10 and L is

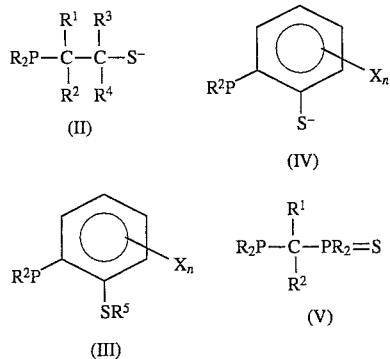

wherein the R groups are independently selected from $C_1$ to $C_{20}$ alkyl, cycloalkyl, aryl, substituted aryl and optionally substituted aralkyl; the $R^5$ groups are selected from hydrogen, $C_1$ to $C_{20}$ alkyl, cycloalkyl, aryl, substituted aryl, aryl and optionally substituted aralkyl groups; the $R^1$ to $R^4$ groups are independently selected from hydrogen, $C_1$ to $C_{20}$ alkyl and optionally substituted aralkyl; X is a non-coordinating substitutent such as $C_1$ to $C_{20}$ alkyl, cycloalkyl, aryl, substituted aryl, $C_1$ to $C_{20}$ alkoxy, $C_1$ to $C_{20}$ alkylthio, trialkylsilyl or triarylsilyl, preferably, $Si(CH_3)_3$ or methyl and n is 0 to 4 preferably 0 or 1.

15 Claims, No Drawings

PROCESS FOR THE CARBONYLATION OF METHANOL OR A REACTIVE DERIVATIVE THEREOF

The present invention relates to a process for the carbonylation of methanol or a reactive derivative thereof in the presence of a halide promoter and a catalyst system comprising a rhodium component and a bidentate phosphorus-sulphur ligand. The present invention also relates to novel rhodium complexes.

The preparation of rhodium (I) and rhodium (II) complexes with mixed sulphur-nitrogen, -phosphorus and -arsenic ligands is described by H. A. Hodali and I. M. Kitranch in *Dirasat:Nat. Sci.* (Univ. Jordan), 1983 10 47–55; CA., 1983 101 16218s.

U.S. Pat. No. 4,670,570 describes a process for the production of carboxylic acids from alcohols in the presence of a catalyst system consisting essentially of rhodium metal atom, a phosphorus containing ligand and a halogen-containing compound as promoter. According to U.S. Pat. No. 4,670,570 in the phosphorus containing ligand at least one oxo (═O) oxygen atom is attached to a phosphorus atom or a carbon atom to form a Z group and the P═O or C═O group in said Z group is located at least one carbon atom removed and preferably from 2–4 carbon atoms removed from the phosphorus atom of the molecules represented by the formulas:

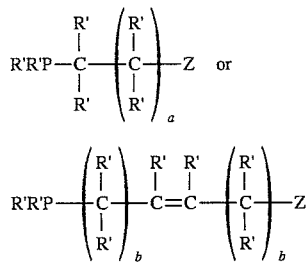

An especially preferred ligand is said to be $Ph_2PCH_2CH_2P(═O)Ph_2$.

International application publication number WO 92/04118 describes novel catalyst precursors having a phosphorus-nitrogen chelated ligand attached to a metal, where said metal is most preferably Rh, Ni or Co. The chelated ligand comprises a substantially unreactive connecting backbone structure which links two different dative centers or a donor with an anionic site. According to WO 92/04118 the catalyst precursor has the general formula:

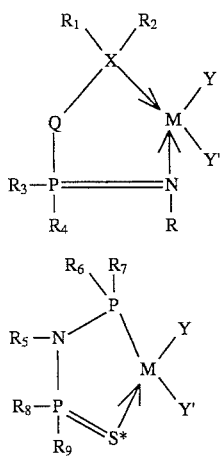

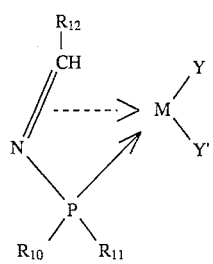

wherein

M is a Group VIII B transition metal

Y,Y' are the same or different selected from CO, Cl$^-$, phosphines and olefinic hydrocarbons, $R_{1-4}$, $R_{6-12}$ are the same or different non-reactive substituents, Q is selected from $(CH_2)_n$ where n=1–5, a benzene ring connected to P and X in the o-positions, an olefin connected to P and X across the double bond, and $(CH_3)CH$ X is P or As R=a substituted aromatic ring,

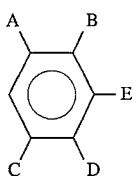

where A, B, C or D are selected from F, H, $NO_2$ and alkyl and E is endocyclic nitrogen or a C—CN group or isomers thereof, or R=SiMe$_3$ or TiCl$_2$Cp where Me is methyl and Cp is cyclopentadiene $R_5$ is aryl or alkyl, and S* is S, Se, O or N—R, R being as defined hereinabove. Amongst the exemplary ligands employed in WO92/04118 are said to be those having the general formulae:

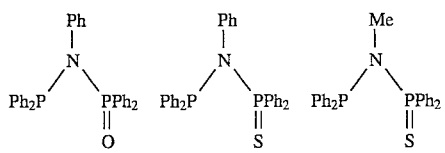

The catalyst precursors described in WO92/04118 are active as catalysts in the carbonylation reaction of methanol to form acetic acid and its derivatives such as methyl acetate. Whilst according to WO 92/04118 the process is said to be performable at 25° C. to 200° C. and the pressure is from 1 psig to 5000 psig, the preferred conditions are said to be 50° C. to 120° C. and 40 to 400 psig and examples are only given at temperatures in the range 80°–90° C. and at a pressure of 40 psig.

The catalyst precursors described in WO92/04118 are not entirely satisfactory.

According to the present invention there is provided a process for the liquid phase carbonylation of methanol or a reactive derivative thereof which process comprises contacting carbon monoxide with a liquid reaction composition comprising methanol or a reactive derivative thereof, a halogen promoter and a rhodium catalyst system comprising a rhodium component and a bidentate phosphorus-sulphur ligand, the ligand comprising a phosphorus dative center linked to a sulphur dative or anionic center by a substantially unreactive backbone structure comprising two connecting carbon atoms or a connecting carbon and a connecting phosphorus atom.

In one preferred embodiment, the phosphorus and sulphur dative centers or phosphorus dative center and anionic sulphur center are linked via two connecting carbon atoms in the backbone structure which backbone structure may comprise an unbranched hydrocarbyl group —CH$_2$—CH$_2$—, a branched hydrocarbyl group such as (CH$_3$)CHCH$_2$ or an unsaturated hydrocarbyl group such as a benzene ring (optionally substituted with a non-coordinating substituent such as —Si(CH$_3$)$_3$ or —CH$_3$) connected in the ortho-positions to the phosphorus and sulphur atoms of the ligand. Alternatively, the phosphorus and sulphur dative centers or the phosphorus dative center and the anionic sulphur center are linked via a connecting carbon and a connecting phosphorus atom in the backbone structure.

Preferably, the bidentate phosphorus-sulphur ligand has a general formula I, II, III, IV or V:

$$R_2P-\underset{R^2}{\overset{R^1}{C}}-\underset{R^4}{\overset{R^3}{C}}-SR^5 \quad (I)$$

$$R_2P-\underset{R^2}{\overset{R^1}{C}}-\underset{R^4}{\overset{R^3}{C}}-S^- \quad (II)$$

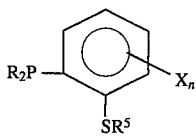
(III)

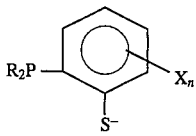
(IV)

$$R_2P-\underset{R^2}{\overset{R^1}{C}}-PR_2=S \quad (V)$$

wherein the R groups are independently selected from C$_1$ to C$_{20}$ alkyl, cycloalkyl, aryl, substituted aryl and optionally substituted aralkyl; the R$^5$ groups are selected from hydrogen, C$_1$ to C$_{20}$ alkyl, cycloalkyl, aryl, substituted aryl, acyl and optionally substituted aralkyl groups; the R$^1$ to R$^4$ groups are independently selected from hydrogen, C$_1$ to C$_{20}$ alkyl and optionally substituted aralkyl; X is a non-coordinating substitutent such as C$_1$ to C$_{20}$ alkyl, cycloalkyl, aryl, substituted aryl, C$_1$ to C$_{20}$ alkoxy, C$_1$ to C$_{20}$ alkylthio, trialkylsilyl or triarylsilyl, preferably, Si(CH$_3$)$_3$ or methyl and n is 0 to 4 preferably 0 or 1. Preferably, the R groups are independently selected from C$_1$ to C$_8$ alkyl, cyclohexyl, phenyl and optionally substituted aryl and the R$^5$ groups are selected from C$_1$ to C$_8$ alkyl, cyclohexyl, phenyl, acetyl and benzyl. Preferably, the R$^1$ to R$^4$ groups are independently selected from hydrogen or C$_1$ to C$_8$ alkyl. Preferably, when n=1, X is —Si(CH$_3$)$_3$ at the 6— position or X is —CH$_3$ at the 4-position.

Examples of preferred ligands are:

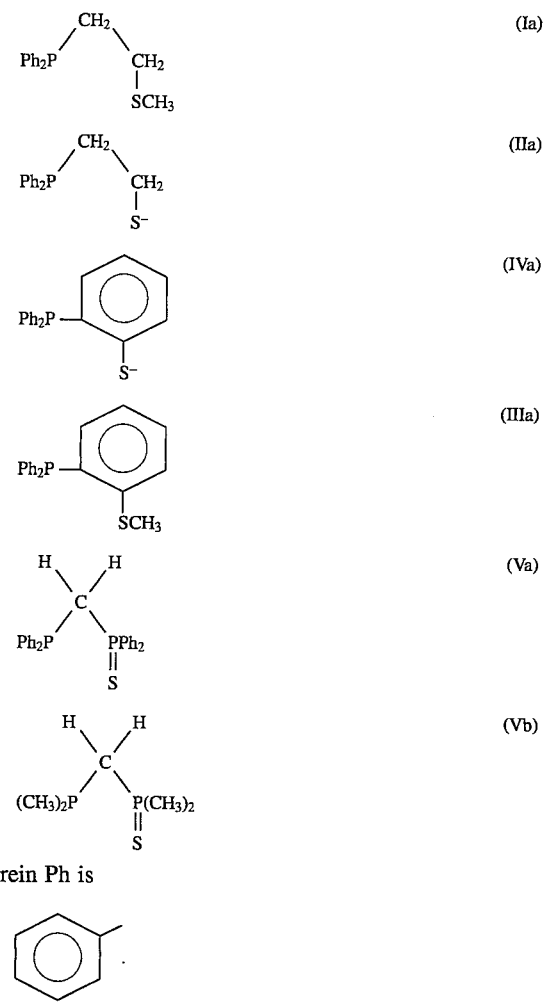

wherein Ph is

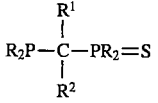

In the process of the present invention, reactive derivatives of methanol include dimethyl ether, methyl acetate and methyl halide, for example, methyl iodide. The products of the process are methyl acetate and/or acetic acid. Preferably, the process according to the present invention is a process for the carbonylation of methanol or a reactive derivative thereof to produce acetic acid.

The process of the present invention is suitably performed at a temperature in the range 25° to 250° C., preferably 50° to 250° C., more preferably 100° to 250° C., yet more preferably 135° to 250° C., and most preferably 145° to 200° C.

The process of the present invention is suitably performed at a pressure in the range 10 to 200 barg, preferably 20 to 200 barg, more preferably 30 to 200 barg and most preferably 50 to 100 barg. Whilst the promotional effect is greatest at higher pressures, economic considerations may dictate the pressure to be used industrially.

Acetic acid may be present as a solvent in the reaction composition in the process of the present invention.

Water may be present in the liquid reaction composition of the process of the present invention, for example, at a concentration in the range 0.1 to 20%, preferably 0.1 to 14% by weight based on the total weight of the liquid reaction composition. The water may be added to the liquid reaction composition and/or may be formed in situ by esterification of methanol with acetic acid solvent and/or acetic acid reaction product present in the liquid reaction composition.

The rhodium component and bidentate phosphorus-sulphur ligand of the catalyst system may be added to the liquid reaction composition of the present invention in the form of a rhodium complex in which the bidentate phosphorus-sulphur ligand is coordinated to rhodium. Preferably, a rhodium component having displaceable groups is premixed with the bidentate phosphorus-sulphur ligand in a suitable inert solvent, for example methanol, prior to addition to the liquid reaction composition. For this $Rh^{III}$ components may not be suitable. With these provisos a rhodium component may be added in any suitable form for example $[Rh(CO)_2Cl]_2$, $[Rh(CO)_2I]_2$, $[Rh(Cod)Cl]_2$, rhodium III chloride, rhodium III chloride trihydrate, rhodium III bromide, rhodium III iodide, rhodium III acetate, rhodium dicarbonylacetylacetonate, $RhCl(PPh_3)_3$ and $RhCl(CO)(PPh_3)_2$.

The rhodium component of the catalyst system may be present in the liquid reaction composition, for example, at a concentration of 25–5000 ppm rhodium and the mole ratio of the rhodium component to the bidentate phosphorus-sulphur ligand is suitably in the range 1:0.5 to 1:4, preferably at a mole ratio of 1:1.

Preferably, the halogen promoter is an organic compound containing iodine, most preferably the halogen promoter is an alkyl iodide, preferably methyl iodide. The concentration of alkyl iodide in the liquid reaction composition is preferably in the range of 1 to 30% by weight, most preferably 5 to 20% by weight.

Also according to the present invention there is provided a rhodium complex having a formula $[Rh(CO)L]_m$ or $[Rh(CO)LY]$ wherein L is a bidentate phosphorus-sulphur ligand having a general formula, (II), (III), (IV) or (V) as hereinbefore defined, preferably (IIa), (IIIa), (IVa), (Va) or (Vb), Y is a halogen, preferably chlorine, bromine or iodine and m is less than 10, typically at least 2.

The invention will now be illustrated by reference to the following examples in which Ph- is

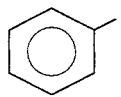

and Me- is $CH_3$-

All preparations were carried out under an atmosphere of nitrogen using standard Schlenk-line techniques. Solvents were dried before use. Unless otherwise stated ligands were characterised by $^{31}P\{^1H\}$ nmr spectroscopy and complexes were characterised by $^{31}P\{^1H\}$ nmr, infrared spectroscopy and microanalysis. NMR spectra were recorded at ambient temperature on a JEOL EX270 spectrometer and were referenced to the $^2H$ lock signal from the solvent with $\Xi_p=40480740$ Hz (idealised value for 85% $H_3PO_4$): positive shifts are downfield. Infrared spectra were recorded on a Perkin-Elmer 1600 Series Fourier Transform spectrometer.

Preparation of Ligands

The ligand bis(diphenylphosphino)methane monosulphide $Ph_2PCH_2P(S)Ph_2$ {Va} was prepared as described in *Can. J. Chem.*, 1988, 66, 1272 by D. E. Berry, J. Browning, K. R. Dixon and R. W. Hilts. The ligand 2-(diphenylphosphino)thiophenol 2-$(Ph_2P)C_6H_4(SH)$ was prepared by the method of E. Block, G. Ofori-Okai and J. Zubieta as described in *J Am. Chem. Soc.*, 1989, 111, 2327 $^{31}P(^1H)$—NMR $(CDCl_3)$: $\delta p=-11.4$ ppm Diphenyl[2-(methylthio)phenyl]phosphine:$^{31}p(1H)$—NMR$(CDCl_3)$: $\delta p=-12.1$ ppm. The ligands $Ph_2PCH_2CH_2P(=O)Ph_2$ and $Ph_2PCH_2P(=O)Ph_2$ were prepared according to the method described in European patent application publication number 0072560. Triphenyl phosphine and $P(=S)Ph_3$ are commercial materials which were obtained from Aldrich.

Preparation of Bis(dimethylphosphino]methane Monosulphide $Me_2PCH_2P(S)Me_2$, (Vb)

A solution of elemental sulphur (0.848 g, 26.5 mmol) in toluene (70 cm$^3$) was added over a period of 5 minutes to a solution of bis(dimethylphosphino)methane (ex Strem; 3.6 g, 26.5 mmol) in toluene (60 cm$^3$) at a temperature of 0° C. The resulting mixture was stirred for 30 minutes at 0° C. at room temperature. Solvent and unreacted bis(dimethylphosphino)methane were removed under reduced pressure to yield a white solid product (2.76 g) comprising a mixture of $Me_2PCH_2P(S)Me_2$ (60% yield based on sulphur) and $Me_2(S)PCH_2P(S)Me_2$ (40% yield).

Preparation of Lithium 2-(diphenylphosphino)ethanethiolate $Ph_2PCH_2CH_2(SLi)$ This preparation is adapted from the procedures described by J. R. Geigy FR 1401930 and J. Chart, J. R. Dilworth, J. A. Schmutz and J. A. Zubieta *J. Chem. Soc. Dalton Trans.*, 1979 1595–99. To a solution of diphenylphosphine (ex Fluka; 0.134 cm$^3$, 0.144 g, 0.772 mmol) in diethyl ether (15 cm$^3$) was added butyllithium (0.31 cm$^3$ of a 2.5M solution in hexanes) and the solution was stirred for 30 minutes at room temperature. Ethylene sulphide (0.46 cm$^3$, 0.109 g, 0.772 mmol) was then added and the mixture was stirred for 2 hours at room temperature. The resulting ethereal solution of lithium 2-(diphenylphosphino)ethanethiolate is suitable for preparing complexes of the 2-(diphenylphosphino)ethanethiolate anion without further treatment. 2-(Diphenylphosphino)ethanethiol: $^{31}p(^1H)NMR(CDCl_3)$: $\delta p=-13.1$ ppm. [2-(Methylthio)ethyl]diphenylphosphine: $^{31}p(^1H)$-NMR$(CDCl_3)$: $\delta p=-13.4$ ppm.

Preparation of Rhodium Catalyst Systems

Preparation of [Rh(CO)LCl]; where L is $Ph_2CH_2P(S)Ph_2$,(Va)

To a solution of $[Rh(CO)_2Cl]_2$ (0.046 g, 0.118 mmol) in methanol (1.9 cm$^3$) was added a slurry of $Ph_2PCH_2P(S)Ph_2$ (0,099 g, 0.237 mmol) in methanol (1.9 ml). Solvent was removed from the resulting mixture under reduced pressure to give an orange solid of product (0.110 g, 80% yield).

Reaction of $[Rh(CO)_2Cl]_2$ with $Me_2PCH_2P(S)Me_2$,(Vb)

To a solution of $[Rh(CO)_2Cl]_2$ (0,092 g, 0.237 mmol) in methanol (3.8 cm$^3$) at a temperature of 0° C. was added a solution of a mixture of $Me_2PCH_2P(S)Me_2$ and $Me_2(S)PCH_2P(S)Me_2$ (0.132 g, containing 0.474 mmol $Me_2PCH_2P(S)Me_2$), prepared as described above, in methanol (3.8 cm$^3$). The resulting mixture (a yellow precipitate in methanol) was used directly as a catalyst for the carbonylation of methanol.

Preparation of Carbonylbis[(P,μ-S)-2-(diphenylphosphino)benzenethiolato]dirhodium(I) Oligomer $([Rh(CO)L]_m$; where L is 2-$(Ph_2P)C_6H_4(S^-)$, IVa)

A mixture of $[Rh(CO)_2Cl]_2$ (0.15 g, 0.385 mmol), 2-(diphenylphosphino)thiophenol (0.22 g, 0.747 mmol) and MeOLi (0.07 g, 1.6 mmol) in methanol (25 cm$^3$) was refluxed for 30 minutes. The resulting red-orange precipitate of product was recovered by filtration (0.287 g, 88% yield). It is now preferred to stir the reagents together for 30 minutes at room temperature instead of refluxing. $C_{19}H_{14}OPRhS$ $M_r$=424.26. Calcd. C 53.79%, H 3.33%: Found C 53.66%, H 3.43%. $^{31}p(^1H)$-NMR (acetone-$d_6$): δp=+60.5 ppm (d,$^1J_{PRh}$ =158 Hz). ν(C≡O)=1946 cm$^{-1}$ (Nujol mull).

Preparation of Carbonylbis
[(P,μ-S)-2)(diphenylphosphino)
ethanethiolato]dirhodium(I) Oligomer ([Rh(CO)L]$_m$;
where L is $Ph_2PCH_2CH_2(S^-)$, IIa)

To a solution of lithium 2-(diphenylphosphino)ethanethiolate (prepared as described above) was added a solution of [Rh(CO)$_2$Cl]$_2$ (0.15 g, 0.386 mmol) in methanol (10 cm$^3$) and the resulting mixture was stirred for 30 minutes. An orange precipitate of product was recovered by filtration (0.264 g, 91% yield). $C_{15}H_{14}OPRhS$ $M_r$= 376.22. Calcd. C 47.89%, H 3.75%: Found C 48.01%, H 3.49%. $^{31}p(^1H)$-NMR (acetone-$d^6$): δp=+63.7 ppm (d,$^1J_{PRh}$=158 Hz) ν(C≡O)=1947 cm$^{-1}$ (Nujol mull).

Preparation of
Chlorocarbonyl[(P,S)-diphenyl(2-(methylthio)phenyl]
phosphine]rhodium(I) ([Rh(CO)LCl]: where L is
2-(Ph$_2$)C$_6$H$_4$(SMe), IIIa)

To a solution of 2-(diphenylphosphino)thiophenol (0.227 g, 0.772 mmol) in methanol (25 cm$^3$), at a temperature of −20° C., was added dropwise iodomethane (0.048 cm$^3$, 0.109 g, 0.772 mmol) over a period of 15 minutes. The solution was allowed to warm to room temperature and [Rh(CO)$_2$Cl]$_2$ (0.15 g, 0.386 mmol) in methanol (10 cm$^3$) was added. The mixture was stirred for 2 hours and a dark brown precipitate of product was recovered by filtration (0.179 g, 49% yield). $C_{20}H_{17}ClOPRhS$ $M_r$=474.75. Calcd. C 50.60%, H 3.61%: Found C 50.88%, H 3.72%. $^{31}p(^1H)$-NMR (CDCl$_3$): δp=+70.3 ppm (d, $^1J_{PRh}$=158 Hz) ν(CD)= 1998 cm$^{-1}$ (Nujol mull)

Preparation of Chlorocarbonyl [(P.
S)-2-methylthio)ethyl)diphenylphosphine]
rhodium(I) ([Rh(COLCl]; where L is $Ph_2PCH_2CH$
(SMe), Ia)

To a solution of lithium 2-(diphenylphosphino)ethanethiolate (prepared as described above) was added dropwise iodomethane (0.048 cm$^3$, 0.109 g, 0.772 mmol) and the mixture was stirred for 2 hours. To this mixture was added a solution of [Rh(CO)$_2$Cl]$_2$ (0.15 g, 0.386 mmol) in methanol (15 cm$^3$) and the mixture was stirred for a further 30 minutes. A dark brown precipitate of product was recovered by filtration (0.191 g, 58% yield). $C_{16}H_{17}ClOPRhS$ $M_r$=426.71. Calcd. c 45.04%, H 4.02%: Found C 44.26%, H 3.61%. $^{31}p(^1H)$-NMR (CDCl$_3$): δp =+72.7 ppm (d, $^1J_{PRh}$= 162 Hz). ν(C≡O)=1984 cm$^{-1}$ (Nujol mull)

General Procedure for Carbonylation of Methanol

Methanol (22.69 g), acetic acid (59.79 g) and methyl iodide (6.84 g) were charged to a 150 cm$^3$ Hastelloy B2 autoclave which was equipped with a Magnedrive (TM) stirrer. The autoclave was then flushed twice with nitrogen and once with carbon monoxide. The reaction mixture was heated under an initial pressure of 1 bara of carbon monoxide to the desired reaction temperature by means of electrical heating coils. The temperature of the reaction mixture was maintained to within 1° C. of the desired reaction temperature by careful control of the amount of heat supplied by the electrical heating coils. A rapid and consistent rate of stirring (1000 rpm) was employed. In a first series of experiments a ligand (1.89×10$^{-3}$ moles) and [Rh(CO)$_2$(Cl)]$_2$ (0.092 g;2.37×10$^{-4}$ moles) were partially or wholly dissolved in methanol (5 g) (see Tables 1 and 2) and the solution or slurry, as the case may be, was injected into the autoclave as the autoclave was simultaneously pressurised with carbon monoxide to a total pressure of 70 barg. In a second series of experiments of rhodium complex (see Table 3) was injected as a solution or slurry in methanol (5 g) into the autoclave as the autoclave was simultaneously pressurised with carbon monoxide to a total pressure of 70 barg. In both series of experiments the pressure in the autoclave was maintained by uptake of carbon monoxide from a ballast vessel and the carbonylation rate was determined by measuring the rate of uptake of carbon monoxide from the ballast vessel. At the end of the reaction, as monitored by uptake of carbon monoxide, the reaction mixture was cooled, the autoclave was vented and a sample of the reaction mixture was analysed by gas chromatography which confirmed the formation of acetic acid during the reaction. The results of carbonylation using different ligands are given in Tables 1 to 3.

TABLE 1

REACTION RATES AT 185° C.

| Experiment | Ligand | Rate$^a$ mol/l/h |
|---|---|---|
| Experiment A | — | 2.3 |
| Experiment B | PPh$_3$ | 2.6 |
| Experiment C | P(=S)Ph$_3$$^b$ | 3.5 |
| Experiment D | Ph$_2$PCH$_2$CH$_2$P(=O)Ph$_2$ | 2.7 |
| Experiment E | Ph$_2$PCH$_2$P(=O)Ph$_2$ | 3.0 |
| Example 1 | Ph$_2$PCH$_2$P(=S)Ph$_2$(Va) | 14.2 |

$^a$The rate is the average rate up to the point at which half of the methanol has been converted to acetic acid.
$^b$Ph(=S)Ph$_3$ was included in the initial autoclave charge and was not present in the solution which was injected into the autoclave.

The results given in Table 1 show that at a temperature of 185° C. the rate of carbonylation of methanol in the presence of triphenylphosphine (a tertiary phosphine ligand; Experiment B) was only marginally higher than the rate in the absence of a phosphine ligand (Experiment A). An improvement in rate was observed in the presence of the monodentate tertiary phosphine sulphide ligand P(=S)PPh$_3$ which was employed in Experiment C. This ligand was also superior in performance to the tertiary bisphosphine monoxide ligands used in Experiments D and E. However, the reaction rate obtained acccording to the present invention in the presence of Ph$_2$PCH$_2$P(=S)Ph$_2$ (a tertiary bisphosphine monosulphide ligand (Example 1)) was 6.2 times that obtained in the absence of a phosphine ligand (Experiment A) and 4.1 times that obtained using the monodentate tertiary phosphine sulphide ligand of Experiment C. Moreover, the carbonylation rate obtained in Example 1 was 4.7 times higher than that obtained in the presence of the corresponding monoxide ligand Ph$_2$PCH$_2$P(=O)Ph$_2$ (Experiment E).

TABLE 2

Reaction Rates at 150° C.

| Example | Ligand | Rate[a]mol/l/h |
|---|---|---|
| Experiment F | $Ph_2PCH_2CH_2P(=O)Ph_2$ | 0.6 |
| Example 2 | $Ph_2PCH_2P(=S)Ph_2(Va)$ | 7.6 |

The results given in Table 2 show that at a temperature of 150° C. the carbonylation rate in the presence of $Ph_2PCH_2P(=S)Ph_2$ is 15 12.7 times that obtained using the monoxide ligand $Ph_2PCH_2CH_2P(=O)Ph_2$.

TABLE 3

Reaction Rates at 185° C.

| Experiment | Complex of Rhodium Component and Ligand | Moles of Complex (×10⁴) | Ligand, L | | Rate mol/l/h |
|---|---|---|---|---|---|
| Example 3 | [Rh(CO)LCl] | 4.74 | $Ph_2PCH_2P(S)Ph_2$ | (Va) | 19.6[a] |
| Example 4 | [Rh(CO)$_2$Cl]$_2$/2L[c] | 2.37 (d) | $Me_2PCH_2P(S)Me_2$ | (Vb) | 12.7[b] |
| Example 5 | [Rh(CO)L]$_m$ | 4.74/m (d) | 2-$(Ph_2P)C_6H_4(S^-)$ | (IVa) | 6.2[a] |
| Example 6 | [Rh(CO)L]$_m$ | 4.74/m (d) | $Ph_2PCH_2CH_2S^-$ | (IIa) | 8.9[a] |
| Example 7 | [Rh(CO)LCl] | 3.38 | 2-$(Ph_2P)C_6H_4(SMe)$ | (IIIa) | 4.2[a] |
| Example 8 | [Rh(CO)LCl] | 3.17 | $Ph_2PCH_2SMe$ | (Ia) | 4.5[a] |
| Experiment A | [Rh(CO)$_2$Cl]$_2$ | 2.37 (d) | — | | 2.3[a] |

[a]The rate is the average rate up to the point at which half of the methanol has been converted to acetic acid.
[b]Initial rate.
[c]Resulting complex was not characterised.
[d]Mole of rhodium = $4.74 \times 10^{-4}$.

The results given in Table 3 show that at a temperature of 85° C., when a rhodium complex having a bidentate phosphorus-sulphur ligand co-ordinated to rhodium is charged to the autoclave (Examples 3 to 8) the rate of carbonylation of methanol is significantly higher than for Experiment A where [Rh(CO)$_2$Cl]$_2$ without a bidentate phosphorus-sulphur ligand was charged to the autoclave.

Experiment G

A carbonylation experiment was performed using the same procedure as for the experiments in Table 3 but using 0.474 mmol of [Rh(CO)LCl] wherein L is $Ph_2PN(Ph)P(S)Ph_2$. Thus, to a solution of [Rh(CO)$_2$Cl]$_2$ (0.092 g, 0.237 mol) in methanol (3.8 cm³) was added a slurry of $Ph_2PN(Ph)P(S)Ph_2$ (0.233 g, 0.473mmol) in methanol (3.8 cm³). The ligand $Ph_2PN(Ph)P(S)Ph_2$ was prepared by the procedure described by M. S. Balakrishna et al in *Inorg. Chem.* 1993 vol 32 5676–5681.

The resulting yellow slurry of

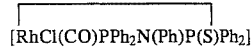
[RhCl(CO)PPh$_2$N(Ph)P(S)Ph$_2$]

formed in the methanol over 5 minutes and was used directly as the catalyst charge in the carbonylation experiment. In the carbonylation experiment, the carbonylation rate (average rate up to the point at which half of the methanol had been converted to acetic acid was 3.4 mol/l/hr which is less than the rates for the ligands according to the present invention in Table 3. The use of $Ph_2PN(Ph)P(S)Ph_2$ in a carbonylation reaction is described in WO 92/04118. This is not an example according to the present invention.

EXAMPLES 9–11

Example 3 was repeated at different pressures and the results are shown in Table 4.

TABLE 4

Reaction Rates at Different Pressures

| Example | Pressure (barg) | Reaction Rate (mol/l/hr)[a] |
|---|---|---|
| 9 | 30 | 14.0 |
| 10 | 50 | 21.2 |

TABLE 4-continued

Reaction Rates at Different Pressures

| Example | Pressure (barg) | Reaction Rate (mol/l/hr)[a] |
|---|---|---|
| 3 | 70 | 19.6 |
| 11 | 100 | 19.8 |

[a]The rate is the average rate up to the point at which half of the methanol has been converted to acetic acid.

We claim:

1. A process for the liquid phase carbonylation of methanol or a reactive derivative thereof which process comprises contacting carbon monoxide with a liquid reaction composition comprising methanol or a reactive derivative thereof, a halogen promoter and a rhodium catalyst system comprising a rhodium component and a bidentate phosphorus-sulphur ligand, the ligand comprising a phosphorus dative center linked to a sulphur dative or anionic center by a substantially unreactive backbone structure comprising two connecting carbon atoms or a connecting carbon and a connecting phosphorus atom.

2. A process as claimed in claim 1 in which the bidentate phosphorus-sulphur ligand is selected from the group consisting of:

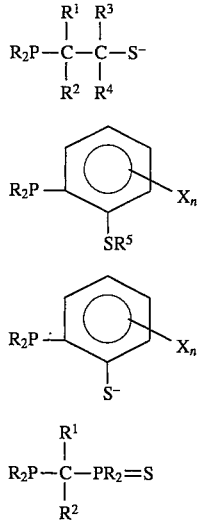

(II)

(III)

(IV)

(V)

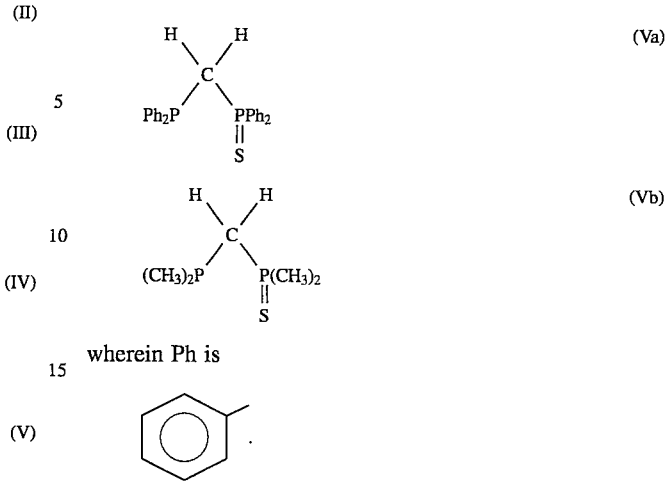

wherein Ph is

[phenyl ring]

wherein the R groups are independently selected from the group consisting of $C_1$ to $C_{20}$ alkyl, cycloalkyl, aryl, substituted aryl and optionally substituted aralkyl; the $R^5$ groups are selected from the group consisting of hydrogen, $C_1$ to $C_{20}$ alkyl, cycloalkyl, aryl, substituted aryl, acyl and optionally substituted aralkyl groups; the $R^1$ to $R^4$ groups are independently selected from the group consisting of hydrogen, $C_1$ to $C_{20}$ alkyl and optionally substituted aralkyl; X is a non-coordinating substituent and n is 0 to 4.

3. A process as claimed in claim 2 in which the R groups are independently selected from the group consisting of $C_1$ to $C_8$ alkyl, cyclohexyl, phenyl and optionally substituted aryl.

4. A process as claimed in claim 2 in which the $R^5$ groups are selected from the group consisting of hydrogen, $C_1$ to $C_8$ alkyl, cyclohexyl, phenyl, acetyl and benzyl.

5. A process as claimed claim 2 in which the $R^1$ to $R^4$ groups are independently selected from the group consisting of hydrogen and $C_1$ to $C_8$ alkyl.

6. A process as claimed in claim 2 in which X is Si $(CH_3)_3$) or methyl.

7. A process as claimed in claim 2 in which the bidentate-sulphur ligand is selected from the group consisting of:

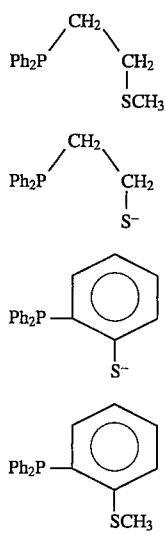

(Ia)

(IIa)

(IIIa)

(IVa)

8. A process as claimed in claim 1, claim 2 or claim 7 in which the process is performed at a temperature in the range of 25° to 250° C. and at a pressure in the range 10 to 200 barg.

9. A process as claimed in claim 8 in which the liquid reaction composition comprises water at a concentration in the range of 0.1 to 20% by weight, an alkyl iodide at a concentration in the range 1 to 30% by weight and a rhodium component at a concentration in the range 25–5000 ppm.

10. A process as claimed in claim 9 in which the mole ratio of the rhodium component to the bidentate phosphorus-sulphur ligand is in the range 1:0.5 to 1:4.

11. A process for the production of acetic acid which process comprises contacting carbon monoxide with a liquid reaction composition comprising methanol or a reactive derivative thereof, a halogen promoter and a rhodium component and a bidentate phosphorus-sulphur ligand, the ligand comprising a phosphorus dative center linked to a sulphur dative or anionic center by a substantially unreactive backbone structure comprising two connecting carbon atoms or a connecting carbon and a connecting phosphorus atom.

12. A process as claimed in claim 11 in which the bidentate phosphorus-sulphur ligand is selected for the group consisting of I, II, III, IV and V as defined in claim 2.

13. A process as claimed in claim 12 in which the bidentate phosphorus-sulphur ligand is selected from the group consisting of Ia, IIa, IIIa, IVa, Va and Vb as defined in claim 7.

14. A process as claimed in claim 13 in which the liquid reaction compostion comprises water at a concentration in the range of 0.1 to 20% by weight, an alkyl iodide at a concentration in the range 1 to 30% by weight and a rhodium component at a concentration in the range 25–5000 ppm.

15. A process as claimed in claim 14 in which the mole ratio of the rhodium component to the bidentate phosphorus-sulphur is in the range 1:0.5 to 1:4.

* * * * *

UNITED STATES PATENT AND TRADEMARK OFFICE
CERTIFICATE OF CORRECTION

PATENT NO. : 5,488,153
DATED : January 30, 1996
INVENTOR(S) : MICHAEL J. BAKER, JONATHAN R. DILWORTH, JOHN G. SUNLEY and NIGEL WHEATLEY It is certified that error appears in the above-indentified patent and that said Letters Patent is hereby corrected as shown below:

On the title page:

In the Abstract first line should read "process for"

In the Abstract, l. 11, "Novel rhodium ligand" should start a new paragraph

In the Abstract, l. 12, formula should read "[RH(CO)LY]"

In the Abstract, l. 13, there should be a colon (:) after "is"

Col. 1, last line, insert the word "or"

Col. 5, l. 67 change "(1H)" to --31p( H)--.

Col. 6, lines 12-13, after"0°C." and before "at" insert "and then for 1 hour"

Col. 6, l. 42, correct the formula to read --$Ph_2PCH_2P(S)Ph_2$, (Va)--

Col. 6, l. 46, should read "(0.099 g,"

UNITED STATES PATENT AND TRADEMARK OFFICE
CERTIFICATE OF CORRECTION

PATENT NO. : 5,488,153

DATED : January 30, 1996

INVENTOR(S) : MICHAEL J. BAKER, JONATHAN R. DILWORTH, JOHN G. SUNLEY and NIGEL WHEATLEY It is certified that error appears in the above-indentified patent and that said Letters Patent is hereby corrected as shown below:

Col. 6, l. 52, should read "(0.092 g,"

Col. 7, l. 6, should read "(acetone-$d^6$)"

Col. 7, l. 11, should read "-2-"

Col. 7, l. 27, should read "($Ph_2P$)"

Col. 7, l. 39, should read --v (c=o)=--.

Col. 7, l. 44, change "COLCl" to --(CO)LCl and correct the formula of --$Ph_2PCH_2CH_2$--

Signed and Sealed this

Thirtieth Day of July, 1996

Attest:

*Attesting Officer*

BRUCE LEHMAN

*Commissioner of Patents and Trademarks*